United States Patent [19]

Pogell et al.

[11] 4,283,391

[45] Aug. 11, 1981

[54] PAMAMYCIN

[75] Inventors: Burton M. Pogell, St. Louis, Mo.; Pamela A. McCann, Flemington, N.J.

[73] Assignee: St. Louis, University, St. Louis, Mo.

[21] Appl. No.: 57,795

[22] Filed: Jul. 16, 1979

Related U.S. Application Data

[63] Continuation-in-part of Ser. No. 964,952, Nov. 30, 1978, abandoned.

[51] Int. Cl.³ ............................................. A61K 35/00
[52] U.S. Cl. ................................................... 424/122
[58] Field of Search ......................................... 424/122

[56] References Cited

U.S. PATENT DOCUMENTS 2,763,642  9/1956  Porter et al. .......................... 424/180

OTHER PUBLICATIONS

McCann et al., Abstracts of Am. Society of Microbiology (1977) p. 176.
Pogell, Third International Symposium on the Genetic of Industrial Microorganism, Madison, Wisconsin, Jun. 4-9, 1978.
McCann et al., J. of Antibiotics, Pamamycin, A new Antibiotic and Stimulator of aerial Mycelia Formation, vol. 32, No. 7, Jul. 1979, pp. 673-678.

*Primary Examiner*—Jerome D. Goldberg
*Attorney, Agent, or Firm*—John S. Roberts, Jr.

[57] ABSTRACT

A new antibiotic named pamamycin is derived from *S. alboniger*. The antibiotic compound is neutral and terpene-like as derived from *S. alboniger*. The antibiotic is produced in conjunction with substances which either stimulate or inhibit the transition of substrate to aerial mycelia. Pamamycin may be separated by thin layer chromatography. The antibiotic displays particular $R_f$ values in thin layer chromatography as well as a particular antimicrobial spectrum for its use. The molecular formula is 621 and the elemental formula thereof is $C_{36}H_{63}NO_7$ as determined by mass spectroscopy. The structure is believed to be a saturated alkane and terpene-like. In vivo tests with *Staphylococcus aureus* indicate that pamamycin is a potent inhibitor of both DNA and RNA synthesis and this antibiotic has present utility in a 1% solution to degerminate hospital walls.

1 Claim, 2 Drawing Figures

NMR SPECTRUM OF PAMAMYCIN.

PAMAMYCIN

The invention described herein was made in the course of work under a grant or award from the Department of Health, Education, and Welfare.

This is a continuation-in-part application of pending Ser. No. 964,952 filed Nov. 30, 1978 now abandoned.

This invention relates to a new antibiotic named pamamycin derived from *S. alboniger*. The antibiotic compound is neutral and terpene-like and is produced as a substance which stimulates the transition of substrate to aerial mycelia. Pamamycin may be separated by thin layer chromatography. The antibiotic displays particular $R_f$ values in thin layer chromatography as well as a particular antimicrobial spectrum for its use. The structure is believed to be a saturated alkane and terpene-like. In vivo tests with *Staphylococcus aureus* indicate that pamamycin is a potent inhibitor of both DNA and RNA synthesis.

Pamamycin is a hydrophobic, neutral compound, insoluble in water but soluble in a wide range of organic solvents including hexanes, ether, benzene, chloroform, methanol, and dimethyl sulfoxide. The molecular weight of purified pamamycin was determined to be 621 by field desorption mass spectroscopy. The elemental composition of this mass ion, $C_{36}H_{63}NO_7$, and other major fragments listed in Table 1 were determined by peak matching and by computer analysis of the high resolution numbers.

TABLE 1

Pamamycin Fragments Obtained by Mass Spectroscopy

| Fragment Mass | Molecular Formula |
| --- | --- |
| 621 | $C_{36}H_{63}NO_7$ |
| 578 | $C_{33}H_{56}NO_7$ |
| 508 | $C_{30}H_{54}NO_5$ |
| 352a | $C_{22}H_{42}NO_2$ |
| 352b | $C_{20}H_{34}NO_4$ |
| 254 | $C_{16}H_{32}NO$ |
| 227 | $C_{13}H_{23}O_3$ |
| 184 | $C_{11}H_{22}NO$ |
| 143 | $C_7H_{11}O_3$ |
| 100 | $C_6H_{14}N$ |

The infrared and ultraviolet spectra indicated that pamamycin was highly aliphatic and showed the absence of aromatic, —OH, —NH, and amide groups. Therefore, the nitrogen is probably in a tertiary linkage. A peak at 1725 cm$^{-1}$ indicated the presence of a carbonyl group, but since this peak was not as intense as the hydrocarbon band at 2880–2960 cm$^{-1}$, there are probably only one or two carbonyl groups.

PRIOR ART STATEMENT

U.S. Pat. No. 2,763,642 Porter et al. This antibiotic puromycin was previously isolated from a strain of *S. alboniger*. The characteristics of this antibiotic are radically different from those of the present invention.

Pogell, "Regulation of Aerial Mycelia Formation in Streptomycetes," Third International Symposium on the Genetics of Industrial Microorganisms, Madison, Wisconsin, American Society for Microbiology, Washington, D.C. pages 218–224 (1979).

McCann and Pogell, "Pamamycin: A New Antibiotic and Stimulator of Aerial Mycelia Formation," submitted to Journal of Antibiotics.

McCann, Redshaw, and Pogell, "Mycelial Differentiation Factors and a Related New Antibiotic from *Streptomyces alboniger*," Abstracts of American Society of Microbiology, 1977, p. 176.

GENERAL PREPARATION AND UTILITY

*S. alboniger* was found to produce a specific factor which stimulated aerial mycelia formation and this factor is pamamycin. It was found in tests with this same partially purified factor that there was also an associated antibiotic acitivty denoted pamamycin which was purified and separated.

Purification procedure. Aerial mycelia positive (am+) cells of *S. alboniger* (A.T.C.C. 12461) were grown on dialysis membranes placed over Hickey-Tresner agar. The cells were harvested, freeze-dried, and exhaustively extracted with methanol in a Soxhlet apparatus. This material was evaporated to dryness and then back-extracted into hexane.

The hexane-soluble material was further fractionated by selective elution from a silica gel column with chloroform:methanol (95:5). Purification of this eluant on silica gel thin layer chromatography (TLC) in benzene:methanol (55:45) gave a fraction with an $R_f$ of 0.57 and some 2,000-fold higher in specific activity (on a dry weight basis) than that present in the original cells. The silica gel column also separated the antibiotic pamamycin from two other components which inhibit aerial mycelia formation in *S. alboniger*.

Activity or utility. The present antibiotic is useful as an antibiotic for gram-positive microorganisms such as *Sarcina lutea*, *Bacillus subtilis*, *Staphylococcus aureus*, and *Proteus*, and also for Mycobacteria. In addition, this antibiotic has broad activity as an antifungal agent. It is further noted as a specific example that a 1% solution of pamamycin is used successfully to degerminate hospital walls. Pamamycin is different from puromycin (2,763,642) on the basis of solubility, charge, and thin layer chromatography. The present antibiotic is most active against gram-positive organisms including *Sarcina lutea*, *Staphylococcus aureus*, and *Bacillus subtilis* but is inactive against gram-negative organisms including *Escherichia coli* and Proteus. The antibiotic is also very active against *Mycobacterium phlei*, *Mycobacterium smegmatis*, and *Neurospora crassa*.

Aerial Mycelia Formation

Pamamycin has the unique property of stimulating the formation of aerial mycelia in *Streptomyces alboniger* at very low concentrations (microgram levels). Stimulation of aerial mycelia formation has been associated with increased yields of antibiotics in streptomycetes fermentations.

TABLE 2

Antimicrobial Spectrum of Pamamycin

| Organism | Diameter of Inhibition Zone (mm)[a] | |
| --- | --- | --- |
|  | 2 Units | 4 Units |
| *Sarcina lutea* | 21 | 25 |
| *Bacillus subtilis* | 10 | 14 |
| *Staphylococcus aureus* | 10 | 14 |
| *Proteus mirabilis* |  | <7 |
| *Proteus morganii* |  | <7 |
| *Escherichia coli* |  | <7 |
| *Mycobacterium phlei* | 21[b] |  |
| *Mycobacterium smegmatis* | 23[b] |  |

TABLE 2-continued

| Organism | Diameter of Inhibition Zone (mm)[a] | |
|---|---|---|
| | 2 Units | 4 Units |
| Neurospora crassa | 15[c] | 21[c] |

[a]Assayed on TSA unless otherwise indicated.
[b]Assayed on minimal media containing 0.7% $K_2HPO_4$, 0.3% $KH_2PO_4$, 0.5% $Na_3$ citrate . $2H_2O$, 0.01% $MgSO_4$ . $7H_2O$, 0.1% $(NH_4)_2SO_4$, and adjusted to pH 7.0, plus 0.5% glucose and 1.5% agar.
[c]Assayed on Vogel's Medium N plus 1% sucrose, 4% sorbose, and 1.5% agar.

PAPER CHROMATOGRAPHY $R_f$ values obtained by paper chromatography were as follows:

| Paper Systems | $R_f$ |
|---|---|
| Water saturated n-butanol | 0.85 |
| Water saturated n-butanol plus 2% p-toluenesulfonic acid (p-TSA) | 0.93 |
| Water saturated n-butanol plus 2% p-TSA and 2% piperidine | 0.94 |
| Water saturated methylisobutylketone (MIBK) | 0.70 |
| Water saturated MIBK plus 2% p-TSA | 0.71 |
| Water saturated MIBK plus 2% piperidine | 0.92 |
| 7% NaCl plus 2.5% methylethylketone in water | 0.11 |
| Water:n-propanol 9:1 | 0.27 |
| Water:n-butanol:ethanol 150:13.5:15 | 0.07 |
| Water:methanol:acetone 12:3:1 - adjusted to pH 10.5 with $NH_4OH$ and lowered to pH 7.5 with $H_3PO_4$ | 0.33 |

THIN LAYER CHROMATOGRAPHY $R_f$ values obtained by thin layer chromatography were as follows:

| Solvent System | $R_f$* | |
|---|---|---|
| | Alumina | Silica Gel |
| Chloroform | — | 0 |
| Benzene:ethyl acetate (70:30) | 0.09 | — |
| Ethyl acetate | 0.11 | — |
| Chloroform:methanol (90:10) | — | 0.12 |
| Benzene:methanol (55:45) | | 0.58 |
| Chloroform:methanol (75:25) | | 0.56 |
| Butanol:acetic acid:$H_2O$ (3:1:1) | — | 0.76 |
| Ethyl acetate:methanol (50:50) | 0.5 | |

*$R_f$ values obtained on glass plates

EXAMPLE 1

The stimulatory activity of pamamycin was quantitated by a disc assay on a slightly modified Hickey-Tresner agar, balanced to give more reproducible zones of aerial mycelia stimulation. Discs containing different samples were placed on plates inoculated uniformly with S. alboniger hyphae and incubated at 37°. After 24-48 hours, the zones of aerial mycelia stimulation were clearly visible as circular areas of intense white powder formation. A plot of zone diameter versus log of stimulator concentration gave a linear response curve.

In addition to its role as a streptomycete differentiation effector, pamamycin has very high antimicrobial activities. Routine measurements of pamamycin during purification were carried out by disc diffusion assays against Sarcina lutea. A unit was defined as the amount of material producing a zone of 17 mm diameter. Activities at various stages of purification were expressed as units/mg of dry weight.

The highest yields of pamamycin were obtained from S. alboniger mycelia grown on Hickey-Tresner agar. The dried cells were extracted with methanol in a Sohxlet apparatus and the methanol extracts concentrated by rotary evaporation. The residue was then triturated into a non-polar solvent, either hexane or benzene, to obtain a substantially purified extract.

Figure 1:
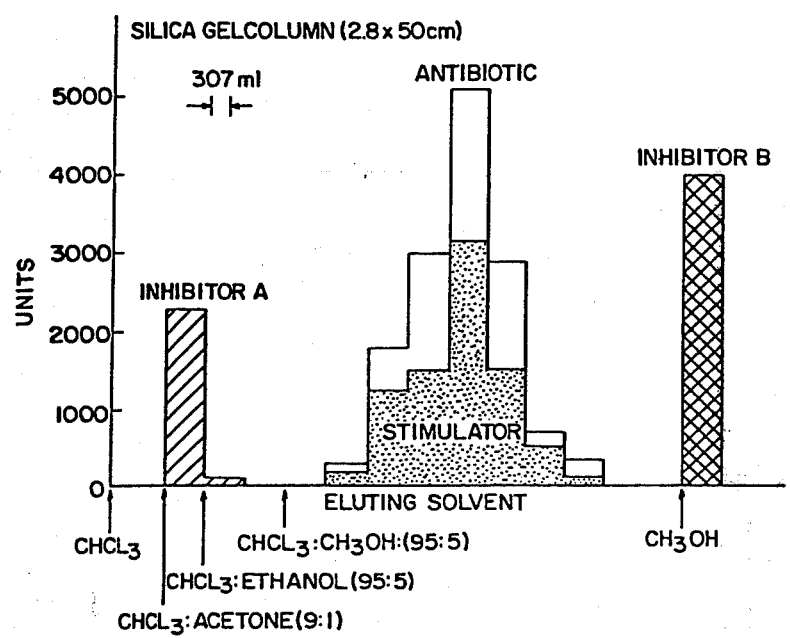
FIG. 1 shows typical results of silicic acid column chromatography with stepwise elution used to separate pamamycin from two inhibitors of aerial mycelia formation.

Silicic acid column chromatography with stepwise elution was then used to separate pamamycin from two inhibitors of aerial mycelia formation. Typical results are illustrated in FIG. 1. Aerial mycelia inhibitor activity was also measured by disc assay against S. alboniger on agar composed of Hickey-Tresner medium minus $CoCl_2$. This deletion enhanced the contrast between the zones of inhibited aerial mycelia and white powdery background. Chloroform eluted the bulk of inactive material, chloroform:acetone (9:1) and chloroform:ethanol (95:5) eluted one major inhibitor component, and chloroform:methanol (95:5) eluted greatly purified pamamycin (329 U/mg). A second distinct fraction containing inhibitor activity was eluted with methanol.

The yields of pamamycin obtained after the silica gel column were relatively constant per unit weight of dry cells (0.64–1.1 U/mg of dried cells). The tremendous increase in yields after the silica gel columns, which varied from 150–2000%, was accounted for by the observation that both of the aerial mycelia inhibitor fractions competitively inhibited pamamycin in a separate Sarcina lutea assay. It was noted during the Sarcina lutea assay that the relative ratios of activities of pamamycin as a stimulator of aerial mycelia formation and inhibitor of Sarcina lutea growth remained constant during purification.

Pamamycin was further purified by column chromatography on neutral alumina and purified to homogeneity by TLC on alumina glass plates in methanol:ethyl acetate ($R_f$=ca. 0.5). The peak fractions had a specific activity of 1000–1200 U/mg.

EXAMPLE 2

Isolation

Pamamycin was obtained from S. alboniger ATCC 12461 mycelia grown on Hickey-Tresner agar. Glass petri dishes (150×15 mm) containing 70 ml agar overlaid with sterile dialysis membrane (A. Thomas, molecular weight cutoff 8000) were inoculated by swabbing from a Hickey-Tresner broth culture (grown 3 days at 28° C., with shaking). After 4–5 days incubation at 28° C., the mycelia were scraped off the membrane, freeze-dried, and stored at −20° C.

Mycelia were extracted with methanol in a Soxhlet apparatus. Methanol extracts were concentrated by rotary evaporation. The residue from 20 g (dry weight) of mycelia was then triturated into a nonpolar solvent, either hexane or benzene, to obtain 580 mg of a substantially purified extract containing pamamycin. This step was carried out in a 50° C. water bath. The pooled extracts were concentrated under $N_2$ gas and any insoluble particles removed by centrifugation at room temperature in a clinical centrifuge (1.29 U/mg).

Silicic acid column chromatography. This step was used to separate pamamycin from two inhibitors of aerial mycelia formation. Silicic acid (Mallinckrodt CC-4, Special for column chromatography) was activated by oven-drying at 105° for 12 hours, cooled in a desiccator, and used within 24 hours. The column was poured in $CHCl_3$, using 150 g silicic acid per g of sample. Chromatography by stepwise elution was carried out as illustrated in FIG. 1 and each eluant fraction concentrated by rotary evaporation. The residues were dissolved in small volumes of toluene and assayed for antibiotic, stimulator, or inhibitor activity. Active fractions of pamamycin (37 mg) were pooled for further purification (432 U/mg dry weight).

Aluminum oxide column chromatography. Aluminum oxide (Woelm Neutral, Brockman Grade I) was deactivated to Grade V by shaking with glass-distilled-deionized water (15 ml per 100 g alumina) and then allowed to stand for 2 hours in a closed container. All solvents used from this point on were freshly redistilled. The pooled silica gel column fractions containing pamamycin activity were concentrated to 150 mg/ml benzene and loaded on the column at a ratio of 1 g of sample per 100 g alumina. Stepwise elution with benzene:-chloroform (70:30, then 60:40) eluted 17.6 mg of relatively pure pamamycin (852 U/mg).

TLC on aluminum oxide. Glass plates (EM, type T, F-254, 250$\mu$ layer) was used for the final step in pamamycin purification. Each plate was prerun in the desired solvent system, air-dried, and then partially deactivated by developing in acetone:water (90:10). After air-drying, the plate was used within 24 hours. Alumina column-purified samples were pooled and spotted on the TLC plate at a concentration of at least 0.4 mg/area of 1 cm d. For final purification, plates were developed in ethyl acetate:methanol (50:50). Active fractions ($R_f$ 0.5, 4.9 mg) were eluted with methanol, triturated into toluene and, if necessary, rerun in the same solvent system for final purification. Peak fractions were filtered through a fine sintered glass plate and used for structural analysis (1,100 U/mg). Similar levels of activity were found in several other preparations. The final toluene extract and washed with water to remove small amounts of impurities.

Pamamycin is a hydrophobic compound, insoluble in water but soluble in a wide range of organic solvents, including hexanes, ether, benzene, chloroform, methanol, and dimethylsulfoxide. It behaved as a neutral compound—the activity could not be extracted from $CHCl_3$ or $CH_2Cl_2$ by 0.1 or 0.5 M acid or base. Heating dry pamamycin above 100° C. destroyed the activity; after 1 hour at 150° C. only 50% of the activity remained. Although purified pamamycin was stable when stored at 4° C. as a toluene solution, it slowly loses activity when stored dry. As much as 14% of the activity was lost after 9 days of storage, and 31% after 21 days.

EXAMPLE 3

Mass Spectroscopy and IR Data

The molecular weight of purified pamamycin was determined to be 621 by field desorption mass spectroscopy. The spectrum indicated the presence of possible homologs with added methylene groups at masses of 635, 649, and 663. The elemental composition of the 621 mass ion ($C_{36}H_{63}NO_7$) and other major fragments listed in Table 1 were determined by peak matching and by computer analysis of the high resolution mass numbers.

The IR spectrum indicated that pamamycin was highly aliphatic and the absence of aromatic, —OH, and —NH groups. There were also no amide I and amide II stretch bands (1600–1700 $cm^{-1}$). Therefore, the nitrogen is probably in a tertiary linkage. A peak at 1725 $cm^{-1}$ indicated the presence of a carbonyl group, but since this peak was not as intense as the CH stretch band at 2880–2960 $cm^{-1}$, there are probably only one or two carbonyl groups. The overall pattern of the IR suggests that the pamamycin is a highly saturated alicyclic compound.

EXAMPLE 4

NMR Data

Figure 2:
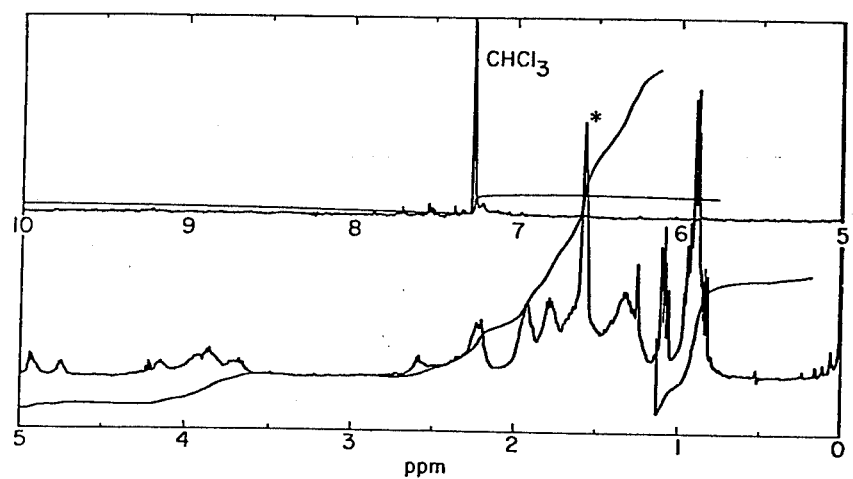
FIG. 2 shows NMR spectrum of pamamycin.

NMR showed no exchangeable hydrogens, confirming the absence of —OH and —NH groups. Referring to FIG. 2, the multiplet centered at approximately 0.9 ppm indicates various methyl groups. The multiplets between 1.25–2.0 ppm and 2.0–2.75 ppm indicate that much of the hydrogen is in methylene and methine groups, respectively. The triplet at 1.1 ppm is consistent with the loss of a propyl group, as seen in the mass spectral fragmentation pattern (fragment 578 results from loss of a propyl group).

We claim:

1. Pamamycin which has an elemental composition of $C_{36}H_{63}NO_7$ and is defined by an NMR spectrum containing no exchangeable hydrogens, a multiplet centered at approximately 0.9 ppm indicating methyl groups, and multiplets in the range between 1.25–2.0 ppm and 2.0–2.75 ppm showing that the bulk of the hydrogen is methine and methylene groups and finally a triplet at 1.1 ppm indicating loss of a propyl group and being characterized by an IR spectrum which is highly aliphatic and showing an absence of aromatic, —OH, and —NH groups, further characterized by a peak at 1725 $cm^{-1}$ indicating a carbonyl group and further characterized by no amide 1 and amide 2 stretch bands (1600–1700 $cm^{-1}$) indicating the nitrogen present is as a tertiary linkage.

* * * * *